(12) United States Patent  (10) Patent No.: US 8,006,320 B1
Rohbani  (45) Date of Patent: Aug. 30, 2011

(54) EAR COVERING APPARATUS AND ASSOCIATED METHOD

(76) Inventor: Freydoon Rohbani, Tarzana, CA (US)

( * ) Notice: Subject to any disclaimer, the term of this patent is extended or adjusted under 35 U.S.C. 154(b) by 278 days.

(21) Appl. No.: 12/381,510

(22) Filed: Mar. 12, 2009

Related U.S. Application Data

(60) Provisional application No. 61/068,979, filed on Mar. 12, 2008.

(51) Int. Cl.
*A42B 1/06* (2006.01)

(52) U.S. Cl. ............................................. 2/209; 128/866

(58) Field of Classification Search .............. 2/209, 423, 2/174; 128/864, 866; 381/370, 371, 374, 381/380; 181/129, 130, 135
See application file for complete search history.

(56) References Cited

U.S. PATENT DOCUMENTS

| | | | |
|---|---|---|---|
| 997,673 A * | 7/1911 | Hegge | 128/866 |
| 4,023,642 A * | 5/1977 | Korn | 181/175 |
| 4,802,245 A | 2/1989 | Miano | |
| 5,243,709 A | 9/1993 | Sheehan | |
| 5,551,090 A | 9/1996 | Thompson | |
| 5,881,393 A * | 3/1999 | Marchello | 2/425 |
| 5,913,309 A * | 6/1999 | Sheehan et al. | 128/846 |

* cited by examiner

*Primary Examiner* — Gary L Welch
*Assistant Examiner* — Andrew W Collins

(57) ABSTRACT

A sanitary ear covering includes at least a first body and alternately a second body formed from deformably resilient material. Each of the first and second bodies may have a circular shape when disposed at an equilibrium position. Each of the first and second bodies may be adapted to conform to the user ear and thereby remain at a substantially stable position during operating conditions. Each of the first and second bodies preferably include an ear-receiving section defining a cup-shaped cavity therein, an outer rim directly coupled to an outer perimeter of the cup-shaped cavity, an ear plug mated to the ear-receiving section and projecting orthogonally inward therefrom, and a strap removably connected to a bottom hemisphere of the outer rim.

15 Claims, 8 Drawing Sheets

EAR COVERING APPARATUS AND ASSOCIATED METHOD

CROSS REFERENCE TO RELATED APPLICATIONS

This application claims the benefit of U.S. Provisional Application No. 61/068,979, filed Mar. 12, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

This invention relates to ear protection covers and, more particularly, to an ear covering apparatus for protecting both the inner and outer ear from exposure to fluids and debris.

PRIOR ART

A very painful ailment that disrupts the lives of millions of Americans is the common ear infection. Extremely prevalent amongst children, ear infections are, in fact, one of the most common childhood illnesses; second only to the common cold. Resulting from a variety of precursors, such as a cold or the flu, most ear infections are typified by the inflammation of the inner ear. In the case of infants and small children, an ear infection often results when fluid and bacteria build up in the area around the baby's eardrum. Normally any fluid that enters this area leaves quickly through the Eustachian tube (which connects the middle ear to the back of the nose and throat) when the baby yawns or swallows. But if the Eustachian tube is blocked—common during colds, sinus infections, even allergy season—it traps the fluid in the middle ear. Bacteria tend to grow in dark, warm, wet places, so a fluid-filled ear becomes the perfect breeding ground. As the infection worsens, so does the swelling in and around the eardrum, and, as a result, the pain. As mentioned, ear infections often occur when fluids back up around the eardrum. Often times, this fluid enters the ear during a routine bath, or even when frolicking in an outdoor kiddy pool.

Accordingly, the present invention is disclosed in order to overcome the above noted shortcomings. The ear covering apparatus is convenient and easy to use, lightweight yet durable in design and designed for protecting both the inner and outer ear from exposure to fluids.

BRIEF SUMMARY OF THE INVENTION

In view of the foregoing background, it is therefore an object of the present invention to provide an apparatus for a sanitary ear covering. These and other objects, features, and advantages of the invention are provided by a sanitary ear covering for prohibiting undesirable fluids and debris from entering a user ear. Such sanitary ear covering preferably includes at least a first body and alternately a second body formed from deformably resilient material. Each of the first and second bodies may have a circular shape when disposed at an equilibrium position. Each of the first and second bodies may be adapted to conform to the user ear and thereby remain at a substantially stable position during operating conditions.

In one embodiment, each of the first and second bodies preferably include an ear-receiving section defining a cup-shaped cavity therein, an outer rim directly coupled to an outer perimeter of the cup-shaped cavity, an ear plug mated to the ear-receiving section and projecting orthogonally inward therefrom, and a strap removably connected to a bottom hemisphere of the outer rim.

The outer rim is preferably formed from a deformably resilient material and is adapted to conform to an outer contour of the user ear during operating conditions. The outer rim may be provided with a gap formed therein. Such an outer rim may also have first and second ends spaced apart at the gap and positioned at a bottom-most region of each of the first and second bodies.

The strap may also be adhesively coupled to the outer rim and span beneath the gap such that the first and second ends maintain a fixed spatial distance therebetween during operating conditions. The strap is adjustably affixed to the outer rim and thereby maintains the outer rim at a substantially stable position while positioned about the user ear. Such a strap preferably remains spaced from the ear-receiving section and spans along an outer perimeter of the outer rim.

The ear-receiving section preferably includes an open medial face receiving the user ear therein. Such an ear-receiving section may further have a maximum diameter at the open medial face and a minimum diameter at a closed lateral face of the ear-receiving section. The closed lateral face may be oppositely spaced from the open medial face. The closed lateral face may be planar and preferably defines an outer-most surface of each of the first and second bodies respectively.

The ear plug may be configured in such a manner that a distal tip of the ear plug terminates prior to reaching the open medial face of the ear-receiving section. Such an ear plug is preferably adapted to fit inside an ear canal of the user.

In one embodiment, the present invention may further include a flexible plate housed inside the cavity, and a first set of fastening members attached to a rear wall of the plate and the closed lateral face respectively. A second set of fastening members may be attached to a front wall of the plate and a proximal end of the ear plug respectively. In this manner, the plate is adjustably and removably affixed to the open lateral face, and the ear plug is adjustably and removably affixed to the plate such that the ear plug adequately sits inside the user ear canal during extended periods of time.

In one embodiment, the present invention may further include an arcuate coupling having opposed ends directly connected to the lateral outer faces of the first and second bodies respectively. Such an arcuate coupling may be adapted to be positioned over a user head during operating conditions.

The present invention further includes a method of utilizing a sanitary ear covering for prohibiting undesirable fluids and debris from entering a user ear. Such a method includes the chronological steps of: providing first and second bodies formed from deformably resilient material, as described hereinabove. For example, each of the first and second bodies may have a circular shape when disposed at an equilibrium position. Each of the first and second bodies may be adapted to conform to the user ear and thereby remain at a substantially stable position during operating conditions.

In one embodiment, each of the first and second bodies preferably include an ear-receiving section defining a cup-shaped cavity therein, an outer rim directly coupled to an outer perimeter of the cup-shaped cavity, an ear plug mated to the ear-receiving section and projecting orthogonally inward therefrom, and a strap removably connected to a bottom hemisphere of the outer rim.

The method may further include the step of positioning the first and second bodies over user ears by situated the respective outer rims about and around the user ears; adjustably positioning the respective ear plugs into user ear canals; and adjustably tensioning the respective straps along the respective outer rims.

The present invention is simple to use, inexpensive, and designed for many years of repeated use. The ear covering apparatus would provide parents of infant and toddler children a practical means of protecting their child's fragile eardrum from exposure to fluids, particularly during bath time or when engaged in aquatic activities. Easily applied, flexible coverings which encompass the ear completely and provide an impenetrable barrier between the ear and external elements, the ear covering apparatus would ensure that water, shampoo and similar fluids would be prevented from seeping into the ear, and thus effectively preventing fluid based ear infections.

Lightweight and comfortable to wear, the baby covering apparatus would easily conform to the shape of the ear via the elastic banding, as well as the rubber seal. Although designed expressly for use during bath time or while engaged in aquatic activities, this cleverly designed product could also be utilized when treating an existing ear infection with medicinal treatments. Providing a sanitary barrier between the inner ear and airborne germs and bacteria, this beneficial product could greatly reduce the recovery time for a variety of ailments.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
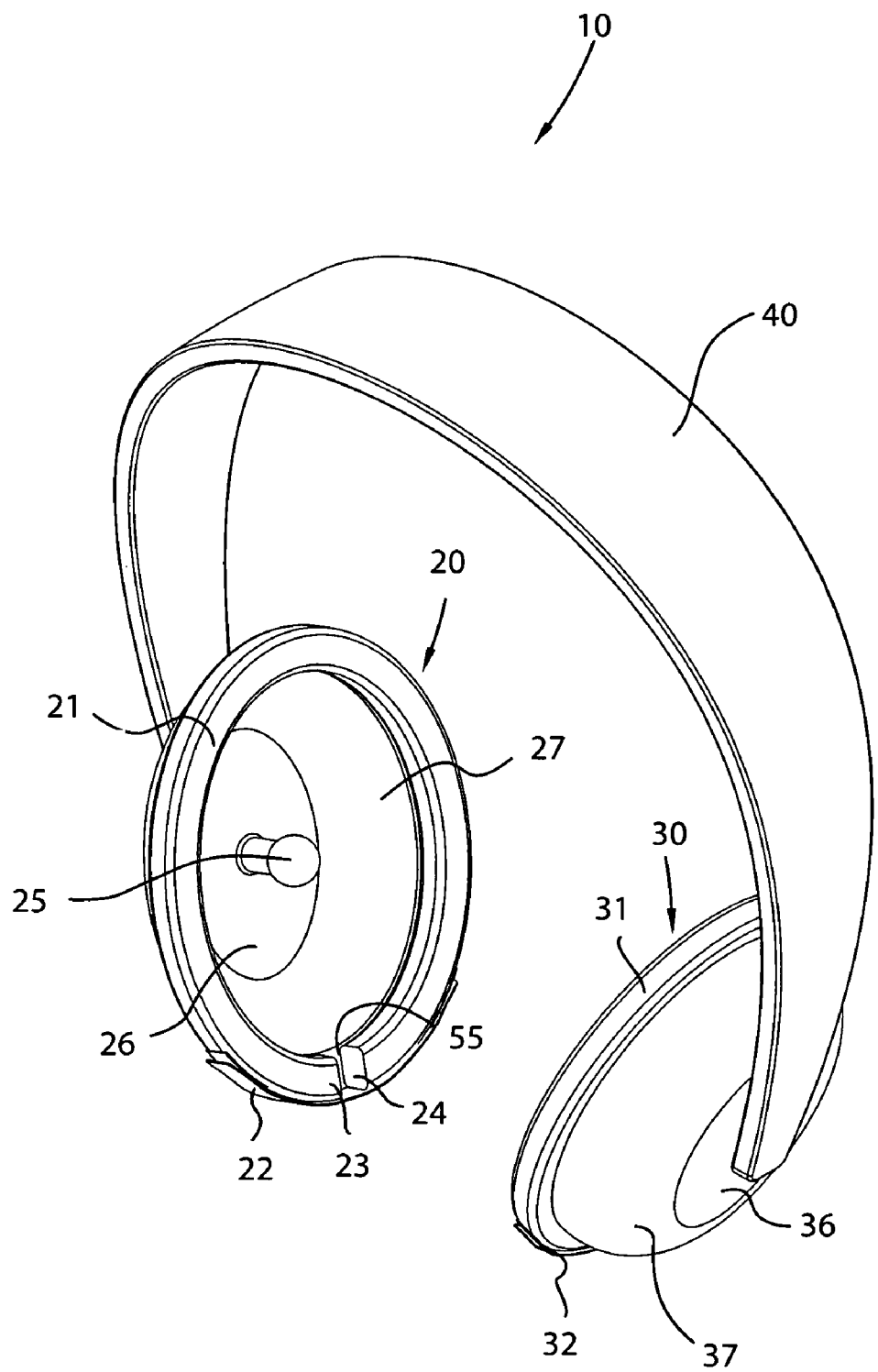
FIGS. 1 and 5 are perspective views showing one embodiment of the present invention, including a coupling attached to the first and second bodies.
Figure 2:
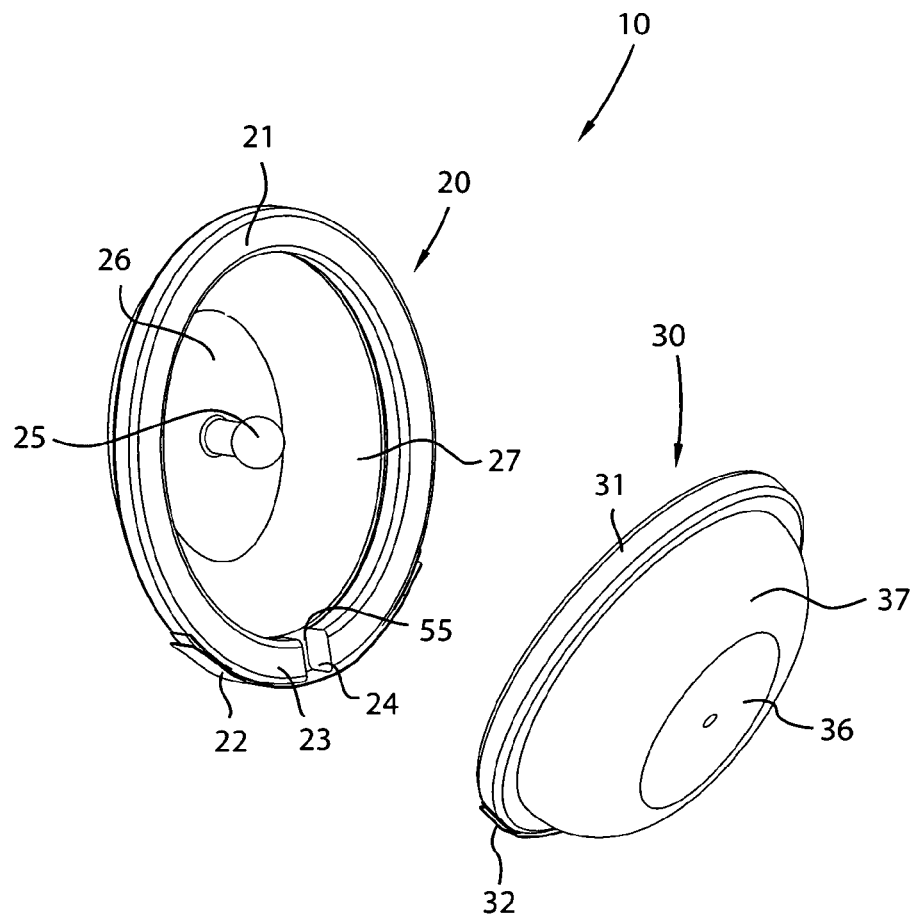
FIGS. 2 and 6 are perspective views showing another embodiment wherein the first and second bodies without the coupling.
Figure 3:
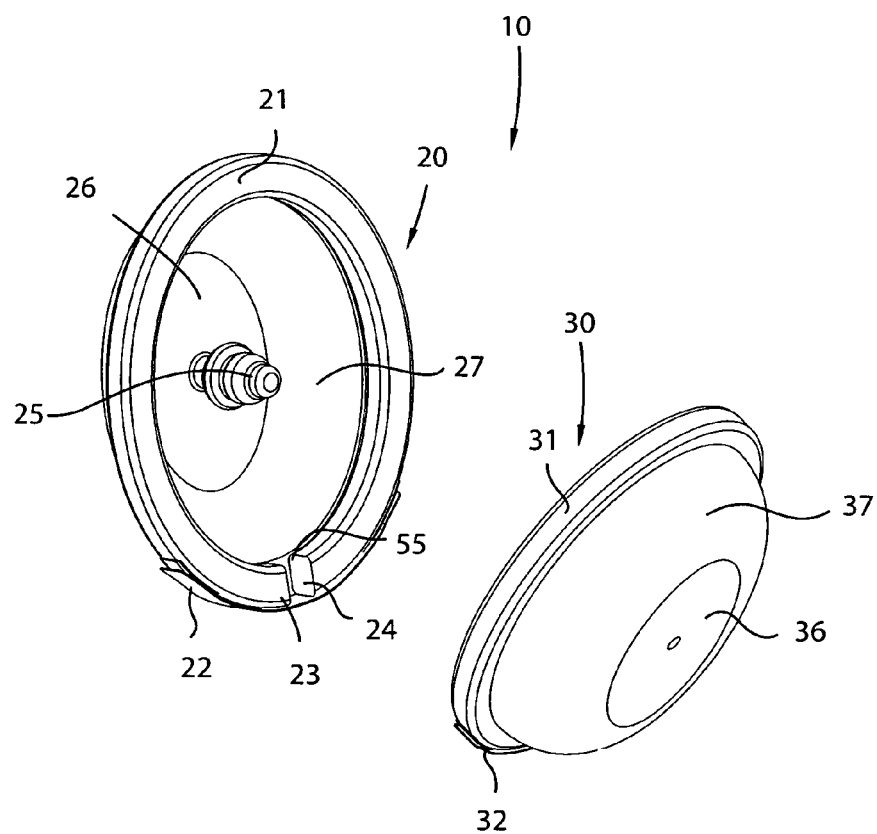
FIGS. 3 and 7 are perspective views showing another embodiment wherein the ear plugs are custom-shaped to mirror an ear canal of a user.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The apparatus of this invention is referred to generally in FIGS. 1-8 by the reference numeral 10 and is intended to provide a protective ear covering apparatus. It should be understood that the protective ear covering apparatus 10 may be used to cover and shield many different types of ears such as both children's ears and adult's ears, for example.

Referring to FIGS. 1-8 in general, the sanitary ear covering 10 prohibits undesirable fluids and debris from entering a user ear. Such a sanitary ear covering 10 preferably includes at least a first body 20 and alternately a second body 30 formed from deformably resilient material. Each of the first and second bodies 20, 30 may have a circular shape when disposed at an equilibrium position. Each of the first and second bodies 20, 30 may be adapted to conform to the user ear and thereby remain at a substantially stable position during operating conditions. It is noted that second body 30 is depicted in a rear perspective view whereas first body 20 is depicted in a front perspective view. However, first and second bodies 20 and 30 are coextensively shaped and therefore, body 30 has the same structural/functional features of body 20.

Each of the first and second bodies 20, 30 preferably includes an ear-receiving section 27 defining a cup-shaped cavity therein, an outer rim 21, 31 directly coupled to an outer perimeter of the cup-shaped cavity, and an ear plug 25 mated to the ear-receiving section 27 and projecting orthogonally inward therefrom. Each body 20, 30 further includes a strap 22, 32 removably connected to a bottom hemisphere of the outer rim 21, 31.

The outer rim 21, 31 is preferably formed from a deformably resilient material and is adapted to conform to an outer contour of the user ear during operating conditions. The outer rim 21, 31 may be provided with a gap 55 formed therein. Such an outer rim 21, 31 may also have first and second ends 23, 24 spaced apart at the gap 55 and positioned at a bottommost region of each of the first and second bodies 20, 30.

The strap 22, 32 may also be adhesively coupled to the outer rim 21, 31 and spans beneath the gap 55 such that the first and second ends 23, 24 maintain a fixed spatial distance therebetween during operating conditions. The strap 22, 32 is adjustably affixed to the outer rim 21, 31 and thereby maintains the outer rim 21, 31 at a substantially stable position while positioned about the user ear. Such a strap 22, 32 preferably remains spaced from the ear-receiving section 27 and spans along an outer perimeter of the outer rim 21, 31.

The ear-receiving section 27 preferably includes an open medial face receiving the user ear therein. Such an ear-receiving section 27 may further have a maximum diameter at the open medial face and a minimum diameter at a closed lateral face 26, 36 of the ear-receiving section 27. The closed lateral face 26, 36 may be oppositely spaced from the open medial face. The closed lateral face 26, 36 may be planar and preferably defines an outer-most surface of each of the first and second bodies 20, 30 respectively.

The ear plug 25 may be configured in such a manner that a distal tip of the ear plug 25 terminates prior to reaching the open medial face of the ear-receiving section 27. Such an ear plug 25 is preferably adapted to fit inside an ear canal of the user. The ear plug 25' may be custom formed to have a predefined shape that mirrors an interior shape of the user's ear canal, as perhaps best shown in FIGS. 3 and 7.

Figure 4:
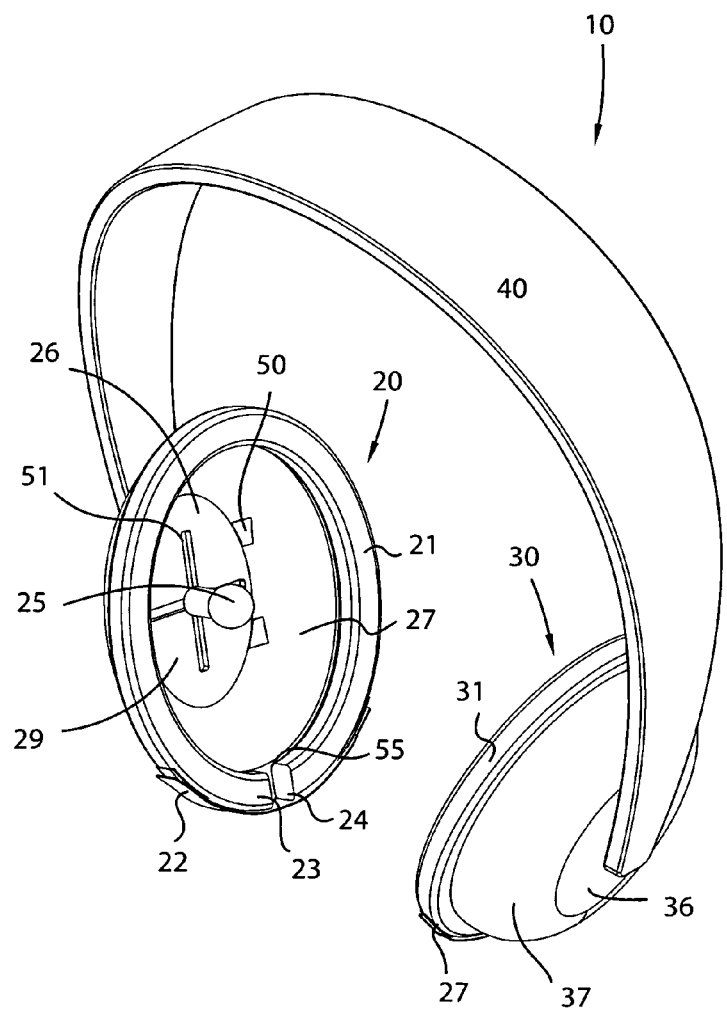
FIGS. 4 and 8 are perspective views showing another embodiment wherein a plate and fastening members are employed to selectively adjust a position of the ear plugs, as needed by the user.
Figure 5:
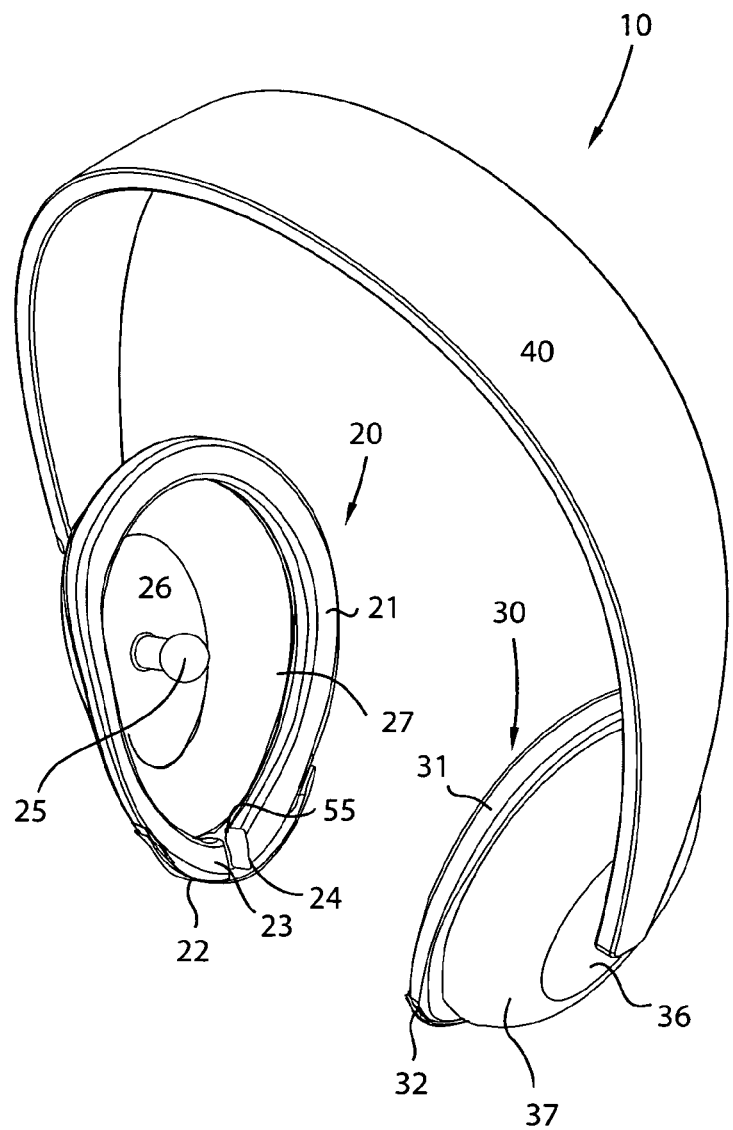
Figure 6:
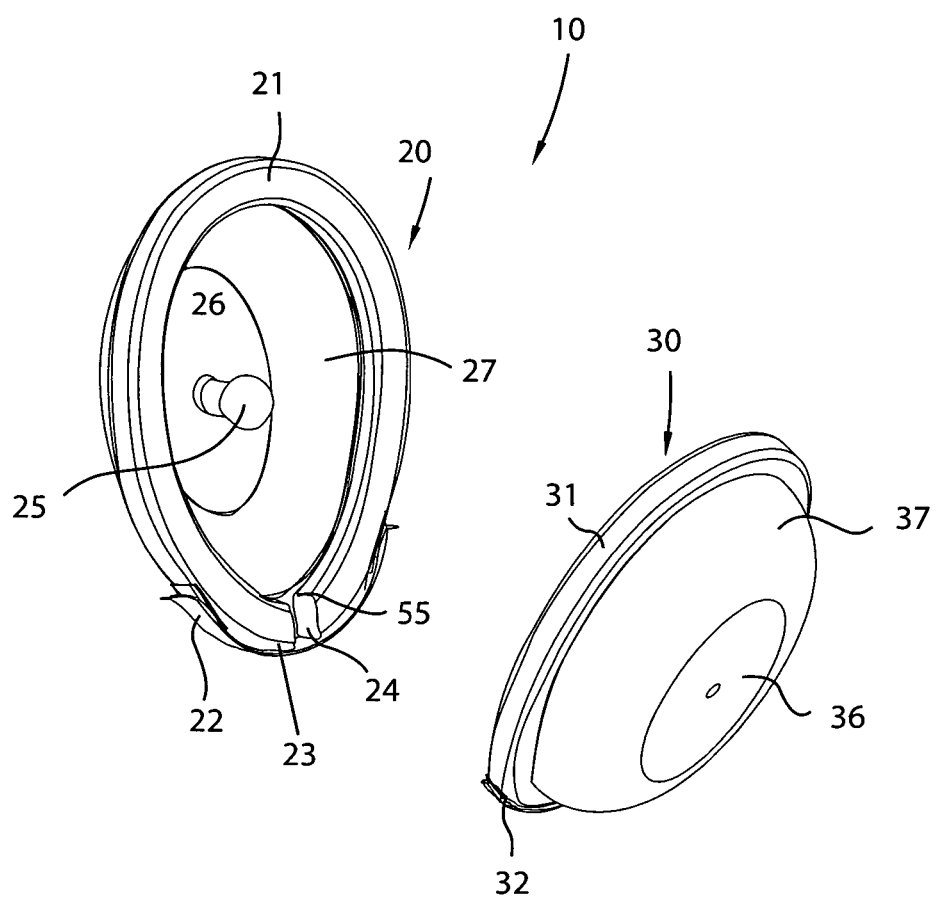
Figure 7:
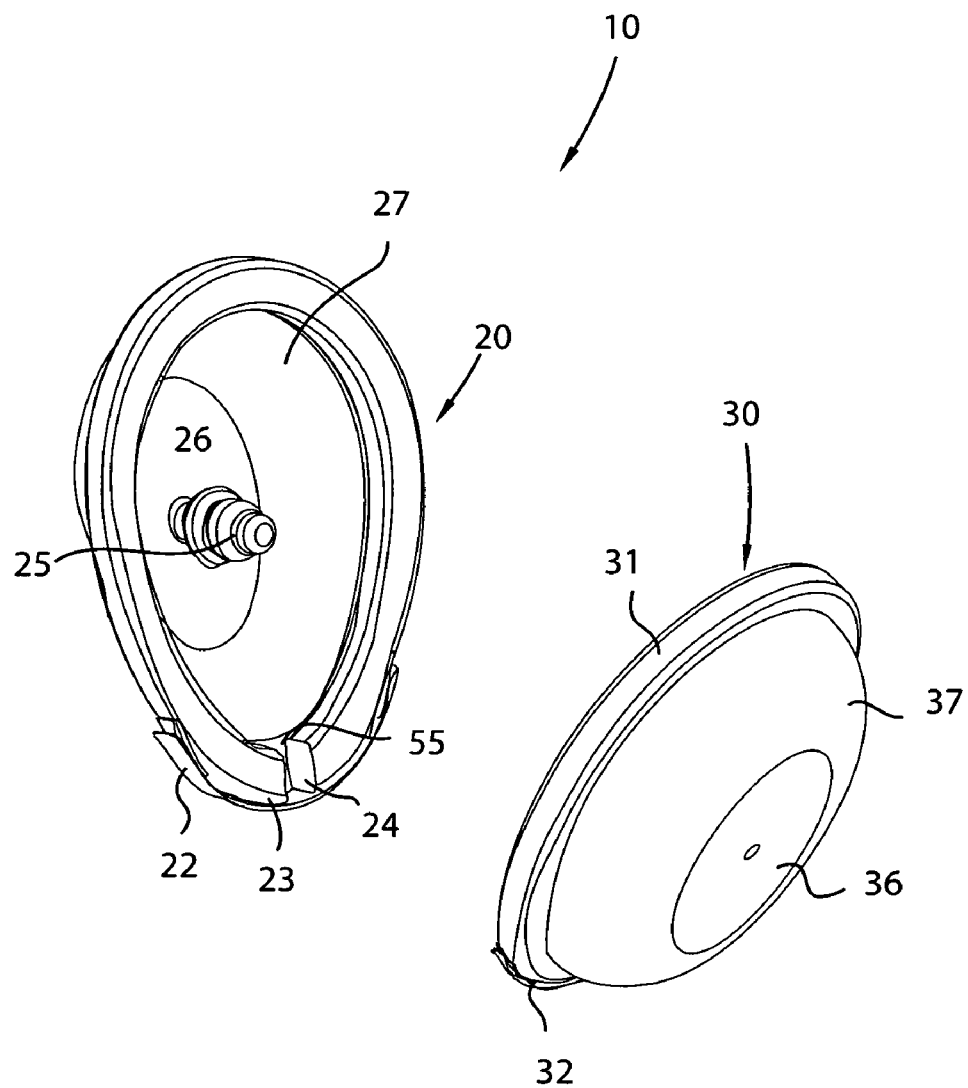
Figure 8:
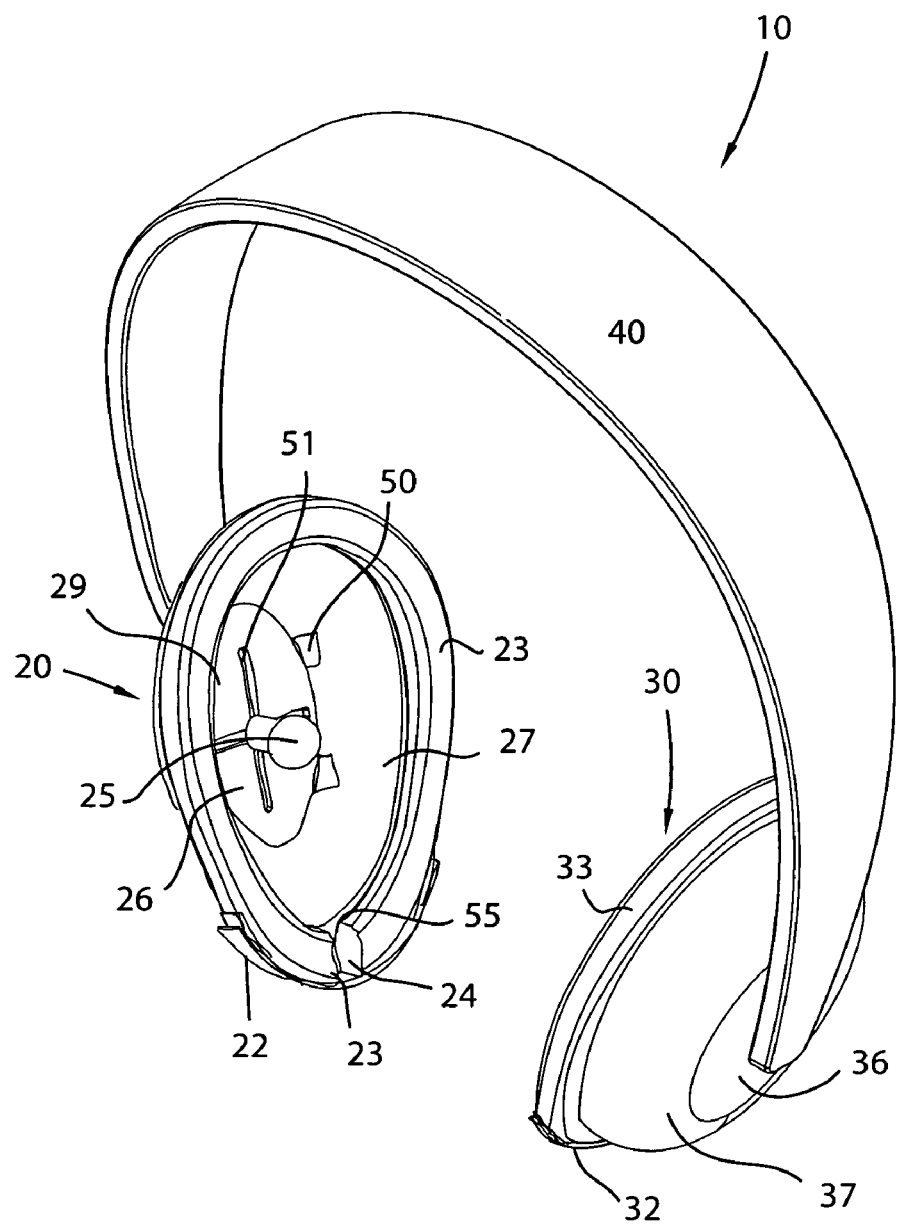

In one embodiment 10", as perhaps best shown in FIGS. 4 and 8, the present invention may further include a flexible plate 29 housed inside the cavity, and a first set of fastening members 50 attached to a rear wall of the plate 29 and the closed lateral face 26 respectively. A second set of fastening members 51 may be attached to a front wall of the plate 29 and a proximal end of the ear plug 25, respectively. In this manner, the plate 29 is adjustably and removably affixed to the open lateral face 26, and the ear plug 25 is adjustably and removably affixed to the plate 29 such that the ear plug 25 adequately sits inside the user ear canal during extended periods of time. In this manner, the position of the ear plug 25 may be selectively adjusted within the ear-receiving section 27 to conform to the user's ear shape and size.

In one embodiment 10', as perhaps best shown in FIGS. 1, 4-5 and 8, the present invention 10' may further include an arcuate coupling 40 having opposed ends directly connected to the lateral outer faces 26, 36 of the first and second bodies 20, 30 respectively. Such an arcuate coupling 40 may be adapted to be positioned over a user head during operating conditions.

The present invention further includes a method of utilizing a sanitary ear covering for prohibiting undesirable fluids and debris from entering a user ear. Such a method includes the chronological steps of: providing first and second bodies 20, 30 formed from deformably resilient material, as described hereinabove. For example, each of the first and second bodies 20, 30 may have a circular shape when disposed at an equilibrium position. Each of the first and second bodies 20, 30 may be adapted to conform to the user ear and thereby remain at a substantially stable position during operating conditions.

Each of the first and second bodies 20, 30 preferably include an ear-receiving section 27, 37 defining a cup-shaped cavity therein, an outer rim 21, 31 directly coupled to an outer perimeter of the cup-shaped cavity, an ear plug 25 mated to the ear-receiving section 27, 37 and projecting orthogonally inward therefrom, and a strap 22, 32 removably connected to a bottom hemisphere of the outer rim 21, 31.

The method may further include the chronological steps of: positioning the first and second bodies 20, 30 over user ears by situating the respective outer rim 21, 31 about and around the user ears; adjustably positioning the respective ear plug 25 into user ear canals; and adjustably tensioning the respective strap 22, 32 along the respective outer rim 21, 31.

Referring to the figures in general, the apparatus 10 effectively prevents fluid from entering a child's ear or an adult's ear, particularly during bath time or when engaged in similar aquatic activities. Bodies 20, 30 wrap around the outer ear, protecting both the outer and inner ear from exposure to the fluids that can lead to painful ear infections. Similar in appearance to individual ear muffs, the ear covering apparatus 10 may be circular in shape and may be manufactured in standard sizes appropriate for wear by infants, toddlers and small children.

In one embodiment, the first and second bodies 20, 30 may measure approximately 2-3" in length, 1-2" in width and approximately ¼-½" in expandable depth. These protective coverings may be manufactured primarily of malleable, waterproof plastic, silicone or rubber material and would feature an expandable depth of 1" (one inch).

Featuring an elastic ear plug 25 at the center of each body 20, 30, the ear covering apparatus would be held securely in place over the ear via the elastic strap 22, 32 as well as by a watertight, rubber outer rim 21, 31 which runs the perimeter of the open medial face. Used individually, the inventor has also designated that the apparatus could be manufactured as a one piece unit, with the two bodies 20, 30 joined together via a flexible fabric or plastic coupling 40 (headband) to be worn over the user's head and scalp. The ear covering apparatus could be produced in a wide variety of vibrant colors, as well as in a host of charming printed designs which would appeal to children and adults.

In one embodiment, use of the ear covering apparatus would be very simple and straight forward. First, a user would select a pair of ear coverings in accordance to design preference. Next, the user would simply hold the first body 20 in both hands, stretching the open medial face 27 so that it encompassed the user's entire outer ear. After the first body 20 is properly positioned, the user would repeat the process with the second body 30. The user could then bathe in the bathtub or shower, or enjoy an afternoon playing beneath a sprinkler or in a pool, assured that their ears would be protected from fluids.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A sanitary ear covering for prohibiting undesirable fluids and debris from entering a user ear, said sanitary ear covering comprising: a first body formed from deformably resilient material, said first body having a circular shape when disposed at an equilibrium position, said first body being adapted to conform to the user ear and thereby remains at a substantially stable position during operating conditions, said first body comprising an ear-receiving section defining a cup-shaped cavity therein;

an outer rim directly coupled to an outer perimeter of said cup-shaped cavity;

an ear plug mated to said ear-receiving section and projecting orthogonally inward therefrom; and a strap removably connected to a bottom hemisphere of said outer rim;

wherein said outer rim is provided with a gap formed therein, said outer rim having first and second ends spaced apart at said gap and being positioned at a bottom-most region of said first body, said strap being adhesively coupled to said outer rim and spanning beneath said gap such that said first and second ends maintain a fixed spatial distance therebetween during operating conditions.

2. The sanitary ear covering of claim 1, wherein said ear-receiving section includes an open medial face receiving the user ear therein, said ear-receiving section further having a maximum diameter at said open medial face and a minimum diameter at a closed lateral face of said ear-receiving section, said closed lateral face being oppositely spaced from said open medial face.

3. The sanitary ear covering of claim 2, wherein said outer rim is formed from deformably resilient material and adapted to conform to an outer contour of the user ear during operating conditions.

4. The sanitary ear covering of claim 3, wherein said ear plug is configured in such a manner that a distal tip of said ear plug terminates prior to reaching said open medial face of said ear-receiving section, said ear plug being adapted to fit inside an ear canal of the user.

5. The sanitary ear covering of claim 4, wherein said strap is adjustably affixed to said outer rim and thereby maintains said outer rim at a substantially stable position while positioned about the user ear, said strap remaining spaced from said ear-receiving section and spanning along an outer perimeter of said outer rim.

6. The sanitary ear covering of claim 5, wherein said closed lateral face is planar and defines an outer-most surface of said first body.

7. The sanitary ear covering of claim 6, further comprising:
a flexible plate housed inside said cavity; and
a first set of fastening members attached to a rear wall of said plate and said closed lateral face respectively;
a second set of fastening members attached to a front wall of said plate and a proximal end of said ear plug respectively;
wherein said plate is adjustably and removably affixed to said open lateral face;
wherein said ear plug is adjustably and removably affixed to said plate such that said ear plug adequately sits inside the user ear canal during extended periods of time.

8. A sanitary ear covering for prohibiting undesirable fluids and debris from entering a user ear, said sanitary ear covering comprising: first and second bodies formed from deformably resilient material, each of said first and second bodies having a circular shape when disposed at an equilibrium position, each of said first and second bodies being adapted to conform to the user ear and thereby remain at a substantially stable position during operating conditions, each of said first and second bodies comprising
an ear-receiving section defining a cup-shaped cavity therein;
an outer rim directly coupled to an outer perimeter of said cup-shaped cavity;
an ear plug mated to said ear-receiving section and projecting orthogonally inward therefrom; and
a strap removably connected to a bottom hemisphere of said outer rim;
wherein said outer rim is provided with a gap formed therein, said outer rim having first and second ends spaced apart at said gap and being positioned at a bottom-most region of each of said first and second bodies, said strap being adhesively coupled to said outer rim and spanning beneath said gap such that said first and second ends maintain a fixed spatial distance therebetween during operating conditions.

9. The sanitary ear covering of claim 8, wherein said ear-receiving section includes an open medial face receiving the user ear therein, said ear-receiving section further having a maximum diameter at said open medial face and a minimum diameter at a closed lateral face of said ear-receiving section, said closed lateral face being oppositely spaced from said open medial face.

10. The sanitary ear covering of claim 9, wherein said outer rim is formed from deformably resilient material and adapted to conform to an outer contour of the user ear during operating conditions.

11. The sanitary ear covering of claim 10, wherein said ear plug is configured in such a manner that a distal tip of said ear plug terminates prior to reaching said open medial face of said ear-receiving section, said ear plug being adapted to fit inside an ear canal of the user.

12. The sanitary ear covering of claim 11, wherein said strap is adjustably affixed to said outer rim and thereby maintains said outer rim at a substantially stable position while positioned about the user ear, said strap remaining spaced from said ear-receiving section and spanning along an outer perimeter of said outer rim.

13. The sanitary ear covering of claim 12, wherein said closed lateral face is planar and defines an outer-most surface of each of said first and second bodies respectively.

14. The sanitary ear covering of claim 13, further comprising:
a flexible plate housed inside said cavity; and
a first set of fastening members attached to a rear wall of said plate and said closed lateral face respectively;
a second set of fastening members attached to a front wall of said plate and a proximal end of said ear plug respectively;
wherein said plate is adjustably and removably affixed to said open lateral face;
wherein said ear plug is adjustably and removably affixed to said plate such that said ear plug adequately sits inside the user ear canal during extended periods of time.

15. The sanitary ear covering of claim 14, further comprising: an arcuate coupling having opposed ends directly connected to said lateral outer faces of said first and second bodies respectively, said arcuate coupling being adapted to be positioned over a user head during operating conditions.

* * * * *